US008974484B2

(12) United States Patent
Alferness et al.

(10) Patent No.: US 8,974,484 B2
(45) Date of Patent: *Mar. 10, 2015

(54) REMOVABLE LUNG REDUCTION DEVICES, SYSTEMS, AND METHODS

(71) Applicant: Spiration, Inc., Redmond, WA (US)

(72) Inventors: Clifton A. Alferness, Redmond, WA (US); Hugo X. Gonzalez, Woodinville, WA (US); David H. Dillard, Grapeview, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,052

(22) Filed: Mar. 6, 2013

(65) Prior Publication Data
US 2013/0345737 A1 Dec. 26, 2013

Related U.S. Application Data

(60) Continuation of application No. 12/828,629, filed on Jul. 1, 2010, now Pat. No. 8,414,655, which is a continuation of application No. 12/428,287, filed on Apr. 22, 2009, now Pat. No. 7,757,692, which is a
(Continued)

(51) Int. Cl.
*A61B 17/12* (2006.01)
*A61M 16/04* (2006.01)

(52) U.S. Cl.
CPC ..... *A61B 17/12104* (2013.01); *A61B 17/12022* (2013.01); *A61B 17/12036* (2013.01); *A61B 17/12172* (2013.01); *A61M 16/0404* (2014.02); *A61B 2017/1205* (2013.01)
USPC .......................................... 606/198

(58) Field of Classification Search
CPC ................. A61B 17/12022; A61B 17/12036; A61B 17/12172; A61B 17/12104; A61B 2017/1205; A61M 16/0404
USPC ......... 606/108, 198, 191, 106, 200; 623/23.65; 128/207.14–207.16, 200.26
See application file for complete search history.

(56) References Cited

U.S. PATENT DOCUMENTS 2,115,298 A 4/1938 Brown
2,728,225 A 12/1955 Skibitzke
(Continued)

FOREIGN PATENT DOCUMENTS

AU 2002239759 5/2002
CA 2308186 5/1999
(Continued)

OTHER PUBLICATIONS

US 8,192,499, 06/2012, Kutsko et al. (withdrawn).
(Continued)

*Primary Examiner* — Pedro Philogene
(74) *Attorney, Agent, or Firm* — Knobbe Martens Olson & Bear LLP

(57) ABSTRACT

An air passageway obstruction device includes a frame structure and a flexible membrane overlying the frame structure. The frame structure is collapsible upon advancement of the device into the air passageway, expandable into a rigid structure upon deploying in the air passageway and recollapsible upon removal from the air passageway. The flexible membrane obstructs inhaled air flow into a lung portion communicating with the air passageway. The device may be removed after deployment in an air passageway by recollapsing the device and pulling the device proximally through a catheter.

17 Claims, 7 Drawing Sheets

Related U.S. Application Data continuation of application No. 10/847,554, filed on May 17, 2004, now abandoned, which is a division of application No. 09/951,105, filed on Sep. 11, 2001, now abandoned.

(56) References Cited

U.S. PATENT DOCUMENTS

| | | |
|---|---|---|
| 2,832,078 A | 4/1958 | Williams |
| 2,981,254 A | 4/1961 | Vanderbilt |
| 3,320,972 A | 5/1967 | High et al. |
| 3,370,305 A | 2/1968 | Goott et al. |
| 3,445,916 A | 5/1969 | Schulte |
| 3,472,230 A | 10/1969 | Forgarty |
| 3,540,431 A | 11/1970 | Modin-Uddin |
| 3,617,060 A | 11/1971 | Iezzi |
| 3,657,744 A | 4/1972 | Ersek |
| 3,671,979 A | 6/1972 | Moulopoulos |
| 3,683,913 A | 8/1972 | Kurtz et al. |
| 3,757,783 A | 9/1973 | Alley |
| 3,760,808 A | 9/1973 | Bleuer |
| 3,788,327 A | 1/1974 | Donowitz et al. |
| 3,874,388 A | 4/1975 | King et al. |
| 3,889,657 A | 6/1975 | Baumgarten |
| 3,962,917 A | 6/1976 | Terada |
| 4,014,318 A | 3/1977 | Dockum et al. |
| 4,040,428 A | 8/1977 | Clifford |
| 4,056,854 A | 11/1977 | Boretos et al. |
| 4,084,268 A | 4/1978 | Ionescu et al. |
| 4,086,665 A | 5/1978 | Poirlier |
| 4,205,282 A | 5/1980 | Gipprich |
| 4,212,463 A | 7/1980 | Repinski et al. |
| 4,218,782 A | 8/1980 | Rygg |
| 4,222,126 A | 9/1980 | Boretos et al. |
| 4,250,873 A | 2/1981 | Bonnet |
| 4,267,839 A | 5/1981 | Laufe et al. |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,393,879 A | 7/1983 | Milgrom |
| 4,402,445 A | 9/1983 | Green |
| 4,403,616 A | 9/1983 | King |
| 4,456,016 A | 6/1984 | Nowacki et al. |
| 4,483,200 A | 11/1984 | Togawa et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,583,541 A | 4/1986 | Barry |
| 4,592,741 A | 6/1986 | Vincent |
| 4,601,465 A | 7/1986 | Roy |
| 4,610,256 A | 9/1986 | Wallace |
| 4,619,246 A * | 10/1986 | Molgaard-Nielsen et al. ............ 128/899 |
| 4,654,027 A | 3/1987 | Dragan et al. |
| 4,654,029 A | 3/1987 | D'Antonio |
| 4,681,110 A | 7/1987 | Wiktor |
| 4,684,363 A | 8/1987 | Ari et al. |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,799,311 A | 1/1989 | Matsutani |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,552 A | 8/1989 | Chaux |
| 4,852,568 A | 8/1989 | Kensey |
| 4,870,975 A | 10/1989 | Cronk et al. |
| 4,877,025 A | 10/1989 | Hanson |
| 4,881,939 A | 11/1989 | Newman |
| 4,888,015 A | 12/1989 | Domino |
| 4,896,668 A | 1/1990 | Popoff et al. |
| 4,908,028 A | 3/1990 | Colon et al. |
| 4,920,978 A | 5/1990 | Colvin |
| 4,934,999 A | 6/1990 | Bader |
| 4,936,823 A | 6/1990 | Colvin et al. |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 4,995,872 A | 2/1991 | Ferrara |
| 5,002,772 A | 3/1991 | Curatolo et al. |
| 5,019,086 A | 5/1991 | Neward |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,111,823 A | 5/1992 | Cohen |
| 5,116,360 A | 5/1992 | Pinchuk et al. |
| 5,116,564 A | 5/1992 | Jansen et al. |
| 5,123,919 A | 6/1992 | Sauter et al. |
| 5,127,412 A | 7/1992 | Csometto et al. |
| 5,135,488 A | 8/1992 | Foote et al. |
| 5,135,531 A | 8/1992 | Shiber |
| 5,147,369 A | 9/1992 | Wagner |
| 5,151,105 A * | 9/1992 | Kwan-Gett ............... 623/1.32 |
| 5,158,548 A | 10/1992 | Lau et al. |
| 5,161,524 A | 11/1992 | Evans |
| 5,171,299 A | 12/1992 | Heitzmann et al. |
| 5,186,711 A | 2/1993 | Epstein |
| 5,197,485 A | 3/1993 | Grooters |
| 5,197,963 A | 3/1993 | Parins |
| 5,197,980 A | 3/1993 | Gorshkov et al. |
| 5,207,702 A | 5/1993 | Pearl |
| 5,226,429 A | 7/1993 | Kuzmak |
| 5,255,687 A | 10/1993 | McKenna |
| 5,275,169 A | 1/1994 | Afromowitz et al. |
| 5,281,229 A | 1/1994 | Neward |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels |
| 5,350,388 A | 9/1994 | Epstein |
| 5,352,240 A | 10/1994 | Ross |
| 5,353,470 A | 10/1994 | Bartlett |
| 5,356,412 A | 10/1994 | Golds et al. |
| 5,358,518 A | 10/1994 | Camilli |
| 5,366,475 A | 11/1994 | Voss et al. |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolbly |
| 5,391,205 A | 2/1995 | Knight |
| 5,392,775 A | 2/1995 | Adkins, Jr. et al. |
| 5,398,844 A | 3/1995 | Zaslavsky |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Andersen et al. |
| 5,413,599 A | 5/1995 | Imachi et al. |
| 5,415,658 A | 5/1995 | Kilpela |
| 5,415,660 A | 5/1995 | Campbell et al. |
| 5,417,226 A | 5/1995 | Juma |
| 5,421,325 A | 6/1995 | Cinberg et al. |
| 5,423,830 A | 6/1995 | Schneebaum et al. |
| 5,445,626 A | 8/1995 | Gigante |
| 5,453,090 A | 9/1995 | Martenez et al. |
| 5,456,689 A | 10/1995 | Kresch et al. |
| 5,459,544 A | 10/1995 | Emura |
| 5,484,444 A | 1/1996 | Braunschweiler et al. |

(56) References Cited

U.S. PATENT DOCUMENTS

| | | |
|---|---|---|
| 5,486,154 A | 1/1996 | Kelleher |
| 5,490,860 A | 2/1996 | Middle et al. |
| 5,499,995 A | 3/1996 | Teirstein |
| 5,500,014 A | 3/1996 | Quijano et al. |
| RE35,225 E | 4/1996 | Herweck et al. |
| 5,503,638 A | 4/1996 | Cooper |
| 5,507,754 A | 4/1996 | Green et al. |
| 5,507,797 A | 4/1996 | Suzuki |
| 5,509,900 A | 4/1996 | Kirkman |
| 5,514,153 A | 5/1996 | Bonutti et al. |
| 5,549,626 A | 8/1996 | Miller et al. |
| 5,549,628 A | 8/1996 | Cooper et al. |
| 5,562,608 A | 10/1996 | Sekins et al. |
| 5,562,641 A | 10/1996 | Flomenblit et al. |
| 5,562,728 A | 10/1996 | Lazarus et al. |
| 5,575,293 A | 11/1996 | Miller et al. |
| 5,593,413 A | 1/1997 | Alexander |
| 5,603,698 A | 2/1997 | Roberts et al. |
| 5,607,469 A | 3/1997 | Frey |
| 5,645,565 A | 7/1997 | Rudd et al. |
| 5,647,857 A | 7/1997 | Anderson et al. |
| 5,649,953 A | 7/1997 | Lefebvre |
| 5,660,175 A | 8/1997 | Dayal |
| 5,662,622 A | 9/1997 | Gore et al. |
| 5,662,713 A | 9/1997 | Andersen et al. |
| 5,669,933 A | 9/1997 | Simon et al. |
| 5,676,671 A | 10/1997 | Inoue |
| 5,683,451 A | 11/1997 | Lenker et al. |
| 5,690,644 A | 11/1997 | Yurek et al. |
| 5,693,089 A | 12/1997 | Inoue |
| 5,697,968 A | 12/1997 | Rogers et al. |
| 5,702,343 A | 12/1997 | Alferness |
| 5,702,409 A | 12/1997 | Rayburn et al. |
| 5,725,519 A | 3/1998 | Penner et al. |
| 5,741,271 A | 4/1998 | Nakao et al. |
| 5,752,522 A | 5/1998 | Murphy |
| 5,752,965 A | 5/1998 | Francis et al. |
| 5,755,770 A | 5/1998 | Ravenscroft |
| 5,763,979 A | 6/1998 | Mukherjee et al. |
| 5,766,134 A | 6/1998 | Lisak et al. |
| 5,769,892 A | 6/1998 | Kingwell |
| 5,772,583 A | 6/1998 | Wright et al. |
| 5,779,649 A | 7/1998 | Herbert |
| 5,782,896 A | 7/1998 | Chen et al. |
| 5,797,907 A | 8/1998 | Clement |
| 5,797,920 A | 8/1998 | Kim |
| 5,797,960 A | 8/1998 | Stevens et al. |
| 5,800,339 A | 9/1998 | Salama |
| 5,803,078 A | 9/1998 | Brauner |
| 5,810,806 A | 9/1998 | Ritchart et al. |
| 5,810,809 A | 9/1998 | Rydell |
| 5,810,837 A | 9/1998 | Hofmann et al. |
| 5,810,855 A | 9/1998 | Rayburn et al. |
| 5,817,101 A | 10/1998 | Fiedler |
| 2,479,805 A | 11/1998 | Sabaratnam |
| 5,830,217 A | 11/1998 | Ryan |
| 5,833,694 A | 11/1998 | Poncet |
| 5,840,081 A | 11/1998 | Andersen et al. |
| 5,851,232 A | 12/1998 | Lois |
| 5,855,587 A | 1/1999 | Hyon |
| 5,855,597 A | 1/1999 | Jayaraman |
| 5,855,601 A | 1/1999 | Bessler et al. |
| 5,865,724 A | 2/1999 | Palmer et al. |
| 5,876,434 A | 3/1999 | Flomenblit et al. |
| 5,876,445 A | 3/1999 | Andersen et al. |
| 5,895,387 A | 4/1999 | Guerrero et al. |
| 5,902,312 A | 5/1999 | Frater et al. |
| 5,911,756 A | 6/1999 | Debry |
| 5,925,063 A | 7/1999 | Khosravi |
| 5,944,738 A | 8/1999 | Amplatz et al. |
| 5,947,997 A | 9/1999 | Pavcnik et al. |
| 5,954,636 A | 9/1999 | Schwartz et al. |
| 5,954,766 A | 9/1999 | Zadno-Azizi et al. |
| 5,957,949 A | 9/1999 | Leonhardt et al. |
| 5,957,978 A | 9/1999 | Blom |
| 5,972,009 A | 10/1999 | Fortier et al. |
| 5,976,158 A | 11/1999 | Adams et al. |
| 5,976,174 A | 11/1999 | Ruiz |
| 5,980,545 A | 11/1999 | Pacala et al. |
| 5,984,965 A | 11/1999 | Knapp et al. |
| 5,989,234 A | 11/1999 | Valerio et al. |
| 6,003,517 A | 12/1999 | Sheffield et al. |
| 6,007,575 A | 12/1999 | Samuels |
| 6,009,614 A | 1/2000 | Morales |
| 6,010,511 A | 1/2000 | Murphy |
| 6,010,525 A | 1/2000 | Bonutti et al. |
| 6,020,380 A | 2/2000 | Killian |
| 6,024,759 A | 2/2000 | Nuss et al. |
| 6,027,525 A | 2/2000 | Suh et al. |
| 6,045,560 A | 4/2000 | McKean et al. |
| 6,051,022 A | 4/2000 | Cai et al. |
| 6,053,877 A | 4/2000 | Banik et al. |
| 6,062,575 A | 5/2000 | Mickel et al. |
| 6,068,635 A | 5/2000 | Gianotti |
| 6,068,638 A | 5/2000 | Makower |
| 6,077,214 A | 6/2000 | Schweich et al. |
| 6,077,291 A | 6/2000 | Das |
| 6,079,413 A | 6/2000 | Baran |
| 6,083,141 A | 7/2000 | Hougen |
| 6,083,255 A | 7/2000 | Laufer et al. |
| 6,086,543 A | 7/2000 | Anderson et al. |
| 6,090,035 A | 7/2000 | Campell et al. |
| 6,090,041 A | 7/2000 | Clark |
| 6,096,027 A | 8/2000 | Layne |
| 6,099,551 A | 8/2000 | Gabbay |
| 6,102,885 A | 8/2000 | Bass |
| 6,102,926 A | 8/2000 | Tartaglia et al. |
| 6,123,663 A | 9/2000 | Rebuffat |
| 6,132,458 A | 10/2000 | Staehle et al. |
| 6,135,729 A | 10/2000 | Aber |
| 6,135,991 A | 10/2000 | Muni et al. |
| 6,141,855 A | 11/2000 | Morales |
| 6,142,957 A | 11/2000 | Diamond et al. |
| 6,146,357 A | 11/2000 | Addis |
| 6,146,384 A | 11/2000 | Lee et al. |
| 6,146,388 A | 11/2000 | McDonald |
| 6,149,664 A | 11/2000 | Kurz |
| 6,162,245 A | 12/2000 | Jayaraman |
| 6,165,179 A | 12/2000 | Cathcart et al. |
| 6,168,614 B1 | 1/2001 | Andersen et al. |
| 6,168,617 B1 | 1/2001 | Blaeser et al. |
| 6,174,307 B1 | 1/2001 | Daniel et al. |
| 6,174,323 B1 | 1/2001 | Biggs et al. |
| 6,183,520 B1 | 2/2001 | Pintauro et al. |
| 6,193,748 B1 | 2/2001 | Thompson et al. |
| 6,200,333 B1 | 3/2001 | Laufer |
| 6,203,551 B1 | 3/2001 | Wu |
| 6,206,918 B1 | 3/2001 | Campbell et al. |
| 6,210,338 B1 | 4/2001 | Afremov et al. |
| 6,213,957 B1 | 4/2001 | Milliman et al. |
| 6,231,587 B1 | 5/2001 | Makower |
| 6,231,589 B1 | 5/2001 | Wessman et al. |
| 6,234,996 B1 | 5/2001 | Bagaoisan et al. |
| 6,238,334 B1 | 5/2001 | Easterbrook, III et al. |
| 6,240,615 B1 | 6/2001 | Kimes et al. |
| 6,241,654 B1 | 6/2001 | Alferness |
| 6,241,678 B1 | 6/2001 | Afremov et al. |
| 6,241,758 B1 | 6/2001 | Cox |
| 6,242,472 B1 | 6/2001 | Sekins et al. |
| 6,245,102 B1 | 6/2001 | Jayaraman |
| 6,258,100 B1 | 7/2001 | Alferness et al. |
| 6,264,700 B1 | 7/2001 | Kilcoyne et al. |
| 6,267,775 B1 | 7/2001 | Clerc et al. |
| 6,270,527 B1 | 8/2001 | Campbell et al. |
| 6,277,083 B1 | 8/2001 | Eggers et al. |
| 6,280,398 B1 | 8/2001 | Ritchart et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,296,639 B1 | 10/2001 | Truckai et al. |
| 6,299,604 B1 | 10/2001 | Ragheb et al. |
| 6,302,893 B1 | 10/2001 | Limon et al. |
| 6,312,407 B1 | 11/2001 | Zadno-Azizi et al. |
| 6,322,522 B1 | 11/2001 | Zimmon |

(56) References Cited

U.S. PATENT DOCUMENTS

| | | |
|---|---|---|
| 6,325,777 B1 | 12/2001 | Zadno-Azizi et al. |
| 6,325,778 B1 | 12/2001 | Zadno-Azizi et al. |
| 6,327,505 B1 | 12/2001 | Medhkour et al. |
| 6,327,772 B1 | 12/2001 | Zadno-Azizi et al. |
| 6,328,689 B1 | 12/2001 | Gonzalez et al. |
| 6,331,183 B1 | 12/2001 | Suon |
| 6,338,728 B1 | 1/2002 | Valerio et al. |
| 6,342,062 B1 | 1/2002 | Suon et al. |
| 6,350,278 B1 | 2/2002 | Lenker et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,425,916 B1 | 7/2002 | Garrison et al. |
| 6,428,561 B1 | 8/2002 | Johansson-Ruden et al. |
| 6,439,233 B1 | 8/2002 | Geertsema |
| 6,440,164 B1 | 8/2002 | DiMatteo et al. |
| 6,447,530 B1 | 9/2002 | Ostrovsky et al. |
| 6,454,727 B1 | 9/2002 | Burbank et al. |
| 6,454,754 B1 | 9/2002 | Frank |
| 6,458,076 B1 | 10/2002 | Pruitt |
| 6,458,153 B1 | 10/2002 | Bailey et al. |
| 6,471,718 B1 | 10/2002 | Staehle et al. |
| 6,471,979 B2 | 10/2002 | New et al. |
| 6,485,407 B2 | 11/2002 | Alferness et al. |
| 6,485,436 B1 | 11/2002 | Truckai et al. |
| 6,488,673 B1 | 12/2002 | Laufer |
| 6,491,706 B1 | 12/2002 | Alferness et al. |
| 6,493,589 B1 | 12/2002 | Medhkour et al. |
| 6,503,272 B2 | 1/2003 | Duerig et al. |
| 6,506,166 B1 | 1/2003 | Hendler et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,540,767 B1 * | 4/2003 | Walak et al. .................. 606/200 |
| 6,540,782 B1 * | 4/2003 | Snyders ........................ 623/2.14 |
| 6,544,192 B2 | 4/2003 | Starr et al. |
| 6,544,291 B2 | 4/2003 | Taylor |
| 6,551,255 B2 | 4/2003 | Van Bladel et al. |
| 6,551,303 B1 | 4/2003 | Van Tassel et al. |
| 6,558,429 B2 | 5/2003 | Taylor |
| 6,568,387 B2 | 5/2003 | Davenport et al. |
| 6,569,166 B2 | 5/2003 | Gonzalez |
| 6,585,639 B1 | 7/2003 | Kotmel et al. |
| 6,589,240 B2 | 7/2003 | Hinchliffe |
| 6,589,256 B2 | 7/2003 | Forber |
| 6,592,594 B2 | 7/2003 | Rimbaugh et al. |
| 6,599,304 B1 | 7/2003 | Selmon et al. |
| 6,599,311 B1 | 7/2003 | Biggs et al. |
| 6,600,307 B2 | 7/2003 | Turski |
| 6,610,043 B1 | 8/2003 | Ingenito |
| 6,620,095 B2 | 9/2003 | Taheri |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,285 B2 | 10/2003 | Gabbay |
| 6,648,897 B2 | 11/2003 | Hamilton |
| 6,669,724 B2 | 12/2003 | Park et al. |
| 6,673,070 B2 | 1/2004 | Edwards et al. |
| 6,679,264 B1 | 1/2004 | Deem et al. |
| 6,682,250 B2 | 1/2004 | Banks |
| 6,682,520 B2 | 1/2004 | Ingenito |
| 6,694,979 B2 | 2/2004 | Deem et al. |
| 6,709,401 B2 | 3/2004 | Perkins et al. |
| 6,712,812 B2 | 3/2004 | Roschak et al. |
| 6,716,208 B2 | 4/2004 | Humes |
| 6,722,360 B2 | 4/2004 | Doshi |
| 6,743,259 B2 | 6/2004 | Ginn |
| 6,746,686 B2 | 6/2004 | Hughes et al. |
| 6,749,606 B2 | 6/2004 | Keast et al. |
| 6,749,658 B1 | 6/2004 | DeVore et al. |
| 6,840,952 B2 | 1/2005 | Saker et al. |
| 6,849,049 B2 | 2/2005 | Starr et al. |
| 6,849,084 B2 | 2/2005 | Rabkin et al. |
| 6,852,108 B2 | 2/2005 | Barry et al. |
| 6,860,847 B2 | 3/2005 | Alferness et al. |
| 6,886,558 B2 | 5/2005 | Tanaka |
| 6,887,256 B2 | 5/2005 | Gilson |
| 6,904,909 B2 | 6/2005 | Andreas et al. |
| 6,911,028 B2 | 6/2005 | Shadduck |
| 6,929,637 B2 | 8/2005 | Gonzalez et al. |
| 6,941,950 B2 | 9/2005 | Wilson et al. |
| 6,951,571 B1 | 10/2005 | Srivastava |
| 6,955,675 B2 | 10/2005 | Jain |
| 6,958,059 B2 | 10/2005 | Zadno-Azizi |
| 6,958,076 B2 | 10/2005 | Acosta et al. |
| 6,989,027 B2 | 1/2006 | Allen et al. |
| 6,997,951 B2 | 2/2006 | Solem et al. |
| 7,011,094 B2 | 3/2006 | Rapacki et al. |
| 7,077,851 B2 | 7/2006 | Lutze et al. |
| 7,086,398 B2 | 8/2006 | Tanaka |
| 7,100,616 B2 | 9/2006 | Springmeyer |
| 7,141,046 B2 | 11/2006 | Perkins et al. |
| 7,169,140 B1 | 1/2007 | Kume |
| 7,175,644 B2 | 2/2007 | Cooper et al. |
| 7,207,946 B2 | 4/2007 | Sirokman |
| 7,232,414 B2 | 6/2007 | Gonzalez |
| 7,252,086 B2 | 8/2007 | Tanaka |
| 7,273,469 B1 | 9/2007 | Chan et al. |
| 7,278,430 B2 | 10/2007 | Kumar |
| 7,344,553 B2 | 3/2008 | Opolski et al. |
| 7,357,795 B2 | 4/2008 | Kaji et al. |
| 7,412,977 B2 | 8/2008 | Fields et al. |
| 7,422,584 B2 | 9/2008 | Loomas et al. |
| 7,434,578 B2 | 10/2008 | Dillard et al. |
| 7,476,203 B2 | 1/2009 | DeVore et al. |
| 7,530,995 B2 | 5/2009 | Quijano et al. |
| 7,533,671 B2 | 5/2009 | Gonzalez et al. |
| 7,637,934 B2 | 12/2009 | Mangiardi et al. |
| 7,691,151 B2 | 4/2010 | Kutsko |
| 7,704,268 B2 | 4/2010 | Chanduszko |
| 7,757,692 B2 * | 7/2010 | Alferness et al. ........ 128/207.15 |
| 7,798,974 B2 | 9/2010 | Sirokman |
| 7,842,010 B2 | 11/2010 | Bonnette et al. |
| 7,842,061 B2 | 11/2010 | Dillard et al. |
| 7,854,228 B2 | 12/2010 | Wilson et al. |
| 7,862,500 B2 | 1/2011 | Khairkhahan et al. |
| 7,875,048 B2 | 1/2011 | Dillard et al. |
| 7,887,585 B2 | 2/2011 | Gonzalez et al. |
| 7,896,887 B2 | 3/2011 | Rimbaugh et al. |
| 7,913,698 B2 | 3/2011 | Barry et al. |
| 7,942,931 B2 | 5/2011 | Gonzalez et al. |
| 8,021,385 B2 | 9/2011 | Alferness |
| 8,043,301 B2 | 10/2011 | Adams et al. |
| 8,079,368 B2 | 12/2011 | Springmeyer |
| 8,136,230 B2 | 3/2012 | Adams et al. |
| 8,177,805 B2 | 5/2012 | Alferness |
| 8,177,809 B2 | 5/2012 | Mavani et al. |
| 8,192,478 B2 | 6/2012 | Khairkhahan et al. |
| 8,257,381 B2 | 9/2012 | Dillard et al. |
| 8,414,655 B2 | 4/2013 | Alferness et al. |
| 8,444,690 B2 | 5/2013 | Gonzalez et al. |
| 8,454,708 B2 | 6/2013 | Kutsko et al. |
| 8,603,127 B2 | 12/2013 | Alferness |
| 2001/0010017 A1 | 7/2001 | Letac et al. |
| 2002/0002401 A1 | 1/2002 | McGuckin, Jr. et al. |
| 2002/0072730 A1 | 6/2002 | McGill et al. |
| 2002/0077564 A1 | 6/2002 | Campbell et al. |
| 2002/0077593 A1 | 6/2002 | Perkins et al. |
| 2002/0077696 A1 | 6/2002 | Zadno-Azizi et al. |
| 2002/0095209 A1 | 7/2002 | Zadno-Azizi et al. |
| 2002/0112729 A1 | 8/2002 | DeVore et al. |
| 2002/0147462 A1 | 10/2002 | Mair et al. |
| 2003/0018327 A1 | 1/2003 | Truckai et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0083730 A1 | 5/2003 | Stinson |
| 2003/0125763 A1 | 7/2003 | McInnes |
| 2003/0127090 A1 | 7/2003 | Gifford et al. |
| 2003/0154988 A1 | 8/2003 | DeVore |
| 2003/0181890 A1 | 9/2003 | Schulze et al. |
| 2003/0181922 A1 | 9/2003 | Alferness |

(56) References Cited

U.S. PATENT DOCUMENTS

| | | |
|---|---|---|
| 2003/0183235 A1 | 10/2003 | Rimbaugh et al. |
| 2003/0195385 A1 | 10/2003 | De Vore |
| 2003/0199888 A1 | 10/2003 | Lutze et al. |
| 2003/0199972 A1 | 10/2003 | Zadno-Azizi et al. |
| 2003/0212412 A1 | 11/2003 | Dillard et al. |
| 2003/0216769 A1 | 11/2003 | Dillard et al. |
| 2003/0225445 A1 | 12/2003 | Derus et al. |
| 2004/0010209 A1 | 1/2004 | Sirokman |
| 2004/0024356 A1 | 2/2004 | Tanaka |
| 2004/0039250 A1 | 2/2004 | Tholfsen et al. |
| 2004/0040555 A1 | 3/2004 | Tanaka |
| 2004/0059263 A1 | 3/2004 | DeVore |
| 2004/0143283 A1 | 7/2004 | Mcgill et al. |
| 2004/0194780 A1 | 10/2004 | Doshi |
| 2004/0206349 A1 | 10/2004 | Alferness et al. |
| 2004/0210248 A1 | 10/2004 | Gordon et al. |
| 2004/0211412 A1 | 10/2004 | Alferness et al. |
| 2004/0211434 A1 | 10/2004 | Loomas et al. |
| 2004/0243140 A1 | 12/2004 | Alferness et al. |
| 2005/0033310 A1 | 2/2005 | Alferness et al. |
| 2005/0080434 A1 | 4/2005 | Chung et al. |
| 2005/0096721 A1 | 5/2005 | Mangin et al. |
| 2005/0137611 A1 | 6/2005 | Escudero et al. |
| 2005/0145253 A1 | 7/2005 | Wilson et al. |
| 2005/0222580 A1 | 10/2005 | Gifford, III et al. |
| 2005/0245894 A1 | 11/2005 | Zadno-Azizi |
| 2005/0267643 A1 | 12/2005 | Dorros et al. |
| 2006/0032497 A1 | 2/2006 | Doshi |
| 2006/0064123 A1 | 3/2006 | Bonnette et al. |
| 2006/0100687 A1 | 5/2006 | Fahey et al. |
| 2006/0200076 A1 | 9/2006 | Gonzalez et al. |
| 2006/0206147 A1 | 9/2006 | DeVore et al. |
| 2006/0235432 A1 | 10/2006 | DeVore |
| 2006/0235467 A1 | 10/2006 | DeVore |
| 2006/0241745 A1 | 10/2006 | Solem |
| 2006/0249164 A1 | 11/2006 | Springmeyer |
| 2006/0270940 A1 | 11/2006 | Tsukashima et al. |
| 2007/0209204 A1 | 9/2007 | Chase et al. |
| 2007/0221230 A1 | 9/2007 | Thompson et al. |
| 2007/0225747 A1 | 9/2007 | Perkins et al. |
| 2008/0015627 A1 | 1/2008 | DeVore |
| 2008/0132989 A1 | 6/2008 | Snow et al. |
| 2008/0188801 A1 | 8/2008 | Bencini et al. |
| 2009/0188508 A1 | 7/2009 | Smith, Jr. |
| 2009/0292262 A1 | 11/2009 | Adams et al. |
| 2010/0082089 A1 | 4/2010 | Quadri et al. |
| 2010/0262071 A1 | 10/2010 | Kutsko et al. |
| 2011/0196295 A1 | 8/2011 | Gonzalez |
| 2011/0201956 A1 | 8/2011 | Alferness |
| 2012/0016376 A1 | 1/2012 | Adams |
| 2012/0073126 A1 | 3/2012 | Adams |
| 2012/0101428 A1 | 4/2012 | Springmeyer |
| 2012/0165856 A1 | 6/2012 | Alferness |
| 2012/0209308 A1 | 8/2012 | Kutsko |
| 2012/0289772 A1 | 11/2012 | O'Connell et al. |
| 2012/0289989 A1 | 11/2012 | Dillard et al. |
| 2013/0190679 A1 | 7/2013 | Springmeyer |

FOREIGN PATENT DOCUMENTS

| | | |
|---|---|---|
| CA | 2375752 | 1/2001 |
| CA | 2401331 | 3/2001 |
| CA | 2408923 | 11/2001 |
| CA | 2603948 | 4/2005 |
| CN | 101868199 | 10/2010 |
| CN | 102058443 | 5/2011 |
| CN | 200780019455.6 | 6/2012 |
| CN | 102579155 | 7/2012 |
| DE | 100 04 979 | 8/2000 |
| EP | 0 665 029 | 8/1995 |
| EP | 0 743 071 | 11/1996 |
| EP | 1 078 601 | 2/2001 |
| EP | 1 151 729 | 11/2001 |
| EP | 1 157 663 | 11/2001 |
| EP | 1 206 276 | 5/2002 |
| EP | 1 198 269 | 10/2009 |
| EP | 1 494 632 | 12/2010 |
| EP | 03 716 212 | 12/2010 |
| EP | 2 353 557 | 8/2011 |
| EP | 10 714 725.8 | 8/2011 |
| EP | 2 416 737 | 2/2012 |
| EP | 2 520 321 | 11/2012 |
| EP | 1 496 790 | 6/2013 |
| EP | 2 641 572 | 9/2013 |
| FR | 2 773 702 | 7/1999 |
| GB | 2 082 071 | 3/1982 |
| GB | 2 324 729 | 11/1998 |
| GB | 2 348 138 | 9/2000 |
| HK | 1153639 | 4/2012 |
| JP | 58-163332 | 9/1983 |
| JP | 60-10740 | 1/1994 |
| JP | H08-19544 | 1/1996 |
| JP | 2003-503162 | 1/2003 |
| JP | 2004-535887 | 12/2004 |
| JP | 2005-527297 | 9/2005 |
| JP | 3742010 | 11/2005 |
| JP | 4387803 B2 | 10/2009 |
| JP | 2011-500171 | 1/2011 |
| JP | 2011-523363 | 8/2011 |
| JP | 2009-503031 | 7/2013 |
| RU | 2140211 | 10/1999 |
| RU | 2440066 | 1/2012 |
| SU | 852321 | 8/1981 |
| SU | 1371700 | 2/1988 |
| SU | 1593651 | 9/1990 |
| WO | WO 88/09683 | 12/1988 |
| WO | WO 90/03152 | 4/1990 |
| WO | WO 92/10725 | 6/1992 |
| WO | WO 94/26175 | 11/1994 |
| WO | WO 95/32018 | 11/1995 |
| WO | WO 96/04875 | 2/1996 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/08441 | 3/1998 |
| WO | WO 98/19633 | 5/1998 |
| WO | WO 98/39047 | 9/1998 |
| WO | WO 98/44854 | 10/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/12011 | 3/2000 |
| WO | WO 00/18329 | 4/2000 |
| WO | WO 00/27292 | 5/2000 |
| WO | WO 00/42950 | 7/2000 |
| WO | WO 00/51500 | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/15604 | 3/2001 |
| WO | WO 01/28433 | 4/2001 |

(56) References Cited

FOREIGN PATENT DOCUMENTS

| WO | WO 01/30266 | 5/2001 |
|---|---|---|
| WO | WO 01/30268 | 5/2001 |
| WO | WO 01/37897 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO 01/66190 | 9/2001 |
| WO | WO 01/70114 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22053 | 3/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069808 | 9/2002 |
| WO | WO 02/069823 | 9/2002 |
| WO | WO 02/087447 | 11/2002 |
| WO | WO 02/094087 | 11/2002 |
| WO | WO 01/95786 | 12/2002 |
| WO | WO 03/022124 | 3/2003 |
| WO | WO 03/030975 | 4/2003 |
| WO | WO 03/003946 | 5/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/079944 | 10/2003 |
| WO | WO 03/088820 | 10/2003 |
| WO | WO 03/094996 | 11/2003 |
| WO | WO 03/099164 | 12/2003 |
| WO | WO 2004/010845 | 5/2004 |
| WO | WO 2004/080347 | 9/2004 |
| WO | WO 2005/013835 | 2/2005 |
| WO | WO 2006/034166 | 3/2006 |
| WO | WO 2006/124822 | 11/2006 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |
| WO | WO 2012/158152 | 11/2012 |

OTHER PUBLICATIONS

U.S. Appl. No. 13/388,621, filed Mar. 29, 2013, Alferness.
Amendment mailed Mar. 3, 2004 in response to Office Action dated Oct. 3, 2003 in the related copending U.S. Appl. No. 09/951,105.
Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.
April et al. "Correction of Funnel-Chest According to Senning-Johnson", Schweiz. Rundchau. Med. (PRAXIS) 79, Nr. 12 (1980) pp. 356-360.
Chest Drains, from webmaster@atroi.ed/cp., from website Mar. 21, 2002; pp. 1-3.
Chest Drains, from webmaster@surgical-tutor.org.uk; from Website on Mar. 21, 2002; pp. 1-3.
Dillard et al.,"Evaluation of a Novel Intra-bronchial Valve Device to Produce Lung Volume Reduction," Poster show at conference in Jun. 2002.
EDO Ceramics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
EWS Endobronchial Watanabe Spigots, Novatech, edited Apr. 17, 2002.
Exploring Chest Drain Options; from webmaster google.com; RNWeb: Continuing Education; from website on Mar. 21, 2002; pp. 1-6.
Harris et al., "The Experimental Production in Dogs of Emphysema with Associated Asthmatic Syndrome by Means of an Intratracheal Ball Valve," J Exp Med 30:1919; 75-88.
Horiuchi et al: Three Cases of Intractable Pneumothorax Treated Successfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
J&J Gateway LLC Web Page: Steps in the Mammotome Surgical Procedure; Surgical Technique, Dec. 28, 2001; p. 1-3.
Jones et al: Closure of a Benign Broncho-Oesophageal Fistula by Endoscopic Injection of Bovine Collagen, Cyanoacrylate Glue and Gelfoam; 1996, pp. 53-55 Aust. n. Z. J.. Surg.
Lewis et al, "Pulmonary Interstitial Emphysema: Selective Bronchial Occlusion with a Swan-Ganz Catheter." Archives of Disease in Childhood, 63:1988, 313-315.
Marco: Bubble Detector, from webmaster@marco.de, from Website on Mar. 21, 2002; pp. 1-3.
Matthew et al. "Selective Bronchial Obstruction for Treatment of Bullous Interstitial Emphysema," J. of Ped. 96:1980, 475-477.
Oasis Dry Suction Chest Drains; Instructions for Use; Atrium Medical Corporation, Hudson New Hampshire, on Mar. 27, 2002,pp. 1-4.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081, vol. 48 No. 11.
Ochsner et al. "Chone-Chondrosternon", Journal of Thoracic Surgery, vol. 8, No. 5, Jun. 1939, pp. 469-511.
Puhakka et al., "Acute Bronchial Obstruction: An Experimental Rabbit Model Study." Int. J. of Pediatric Otorhinolaryngology. 18:1989, 107-118.
Shamberger, "Congenital Chest Wall Deformities" Current Problems in Surgery vol. XXXIII, No. 6, Jun. 1996, pp. 470-543.
SIII Control and Display Modules; from webmaster@stoeckert.de; from website on Mar. 21, 2002, pp. 1-5.
Snider et al., "The Definition of Emphysema: Report of the National Heart Lung and Blood Institute, Division of Lung Diseases Workshop", Am. Ev. Respir. Dis., 132:182-185, 1985.
Tanase, D., et al.: "Investigation of Multi-Sensor Techniques for Cardiac-Output Measurements in Intensive Care," Microtechnology in Medicine and Biology, 2005, 3rd IEEE/EMB, Special Topic Conference, pp. 122-125.
Tube Thoracostomy; from webmaster@merck.com/pubs/manual; from Website Mar. 21, 2003, pp. 1,2.
Understanding Chest Drainage; from webmaster@nursingceu.com; from website on Mar. 21, 2002; pp. 1-15.
Watanabe et al: Bronchial Embolization Using Dental Impression Material in a Case of Pyelo-bronchial Fistula with Candida Fungemia; 1991. Journal of the Japan Society for Bronchology, pp. 607-610.
European Supplemental Search Report in European Appln. No. 00969008.2, dated Feb. 26, 2004, 5 pp.
International Search Report in International application No. PCT/US00/40701, mailed Jan. 25, 2001, 3 pp.
Canadian Office Action dated Apr. 28, 2009 for Canadian Application No. 2,459,702.
Canadian Office Action dated Dec. 14, 2010 for Canadian Application No. 2,459,702.
Canadian Office Action dated Mar. 9, 2010 for Canadian Application No. 2,459,702.
European Search Report in European Appln. No. 02759335.9, dated Jan. 31, 2007.
International Search Report in International application No. PCT/US02/25555, mailed Mar. 19, 2003, 4 pp.

(56) References Cited

OTHER PUBLICATIONS

Extended European Search Report for EP 08 0205468, dated Jul. 28, 2009.
European Examination Report dated Apr. 17, 2012 for EP Application No. 08 022 468.6.
European Examination Report dated Apr. 14, 2010 for EP Application No. 03 71 0804.
European Supplemental Search Report dated Nov. 9, 2009 for EP Application No. 03 71 0804.
European Examination Report dated Dec. 30, 2011 for EP Application No. 03 71 0804.
European Extended Search Report dated Oct. 8, 2012 for EP Application No. 12164169.0.
European Extended Search Report dated Sep. 9, 2013 for EP Application No. 12164169.0.
European Examination Report of Apr. 28, 2011, Application No. 10196887.3-1269.
European Extended Search Report dated Mar. 5, 2013, Application No. 10196887.3-1269.
Australian Office Action of Oct. 29, 2007, Application No. 2003219927.
Canadian Office Action of Apr. 28, 2009, Application No. 2,479,805.
European Notice re Amendment of Application Documents of Jun. 17, 2009, Application No. 03 716 212.0-1265.
European Supplemental Search Report of Feb. 28, 2008, Application No. 03 716 212.0-1265.
European Office Action of Dec. 23, 2008, Application No. 03 716 212.0-1265.
European Office Action of Jan. 8, 2009, Application No. 03716212.0.
European Office Action of Mar. 8, 2013, Application No. 03716212.0.
Japanese Office Action re JP Application No. JP 2009-503031, mailed Mar. 6, 2012, and English translation in 9 pages.
Notice of Reasons for Rejection re JP Application No. JP 2009-503031, mailed on Jul. 10, 2012 in six pages.
Japanese Office Action of Feb. 3, 2009, Application No. 2003-577779.
International Search Report of Jul. 7, 2003, Application No. PCT/US03/05968.
Canadian Office Action dated Nov. 5, 2009, re Application No. 2,484,086 in 2 pages.
International Search Report dated Oct. 1, 2003 re PCT Application No. PCT/US2003/14868.
PCT International Preliminary Report on Patentability from corresponding PCT Application No. PCT/US2004/007721, mailed Nov. 25, 2005.
PCT Search Report and Written Opinion from corresponding PCT Application No. PCT/US2004/007721, dated May 4, 2005.
Canadian Office Action, re CA Application No. 2,648,142, dated Aug. 9, 2013.
Chinese Office Action dated Jun. 4, 2010 re CN Application No. 200780019455.6.
Chinese Office Action dated Sep. 28, 2012 (with translation) re CN Application No. 201110022562.2.
Chinese Office Action dated May 30, 2013 (with translation) re CN Application No. 201110022562.2.
Chinese Search Report dated Jun. 26, 2013 re CN Application No. 201110022562.2.
Japanese Office Action dated Mar. 6, 2012, JP Application No. 2009-503031 w/translation.
Japanese Office Action dated Jul. 2, 2012, JP Application No. 2009-503031 w/translation.
PCT International Search Report from corresponding PCT Application No. PCT/US2007/007923, dated May 20, 2008 in 2 pages.
PCT Preliminary and Written Report from corresponding PCT Application No. PCT/US2007/007923, dated Sep. 30, 2008 in 7 pages.
Russian Office Action, for App. No. 2008139081/14(050381), dated Nov. 24, 2010.
International Preliminary Report on Patentability for Application No. PCT/US2010/030131, dated Mar. 18, 2011.
International Report on Patentability dated Dec. 23, 2009 re PCT/US2008/079650.
International Search Report and Written Opinion for Application No. PCT/US2010/030131, dated Jun. 18, 2010.
International Search Report dated Jan. 30, 2009 re PCT/US2008/079650.
Chinese Office Action dated Mar. 20, 2012 re CN App. No. 200880117320.8.
English Translation of Chinese First Office Action mailed Mar. 20, 2012 for Chinese Patent Application No. 200880117320.8.
Chinese Second Office Action issued Oct. 8, 2012 for Chinese Patent Application No. 200880117320.8.
Chinese Third Office Action issued Mar. 5, 2013 for Chinese Patent Application No. 200880117320.8.
Chinese Decision of Rejection issued Sep. 5, 2013 for Chinese Patent Application No. 200880117320.8.
European Examination Report, re EP Application No. 08 837 761.9, dated Jan. 3, 2013.
European Extended Search Report, re EP Application No. 13166857.6, dated Aug. 26, 2013.
Japanese Notice of Reasons for Rejection, re JP Application No. 2010-529122, dated Jan. 22, 2013.
Japanese Notice of Reasons for Rejection, re JP Application No. 2010-529122, dated Jul. 23, 2013.
Japanese Decision of Rejection, re JP Application No. 2010-529122, mailed Nov. 12, 2013.
International Search Report and Written Opinion for Application No. PCT/US2004/025458, mailed Nov. 30, 2004.
Chinese Office Action, re CN Application No. 2012082800791790, dated Aug. 31, 2012.
European Office Action of Dec. 8, 2010, Application No. 09739872.1.
European Office Action on May 6, 2011, Application No. 09739872.1.
European Examination Report dated Oct. 12, 2011 for EP Application No. 09 739 872.1.
International Search Report and Written Opinion re PCT App. No. PCT/US2011/36549, mailed Sep. 16, 2011.

\* cited by examiner

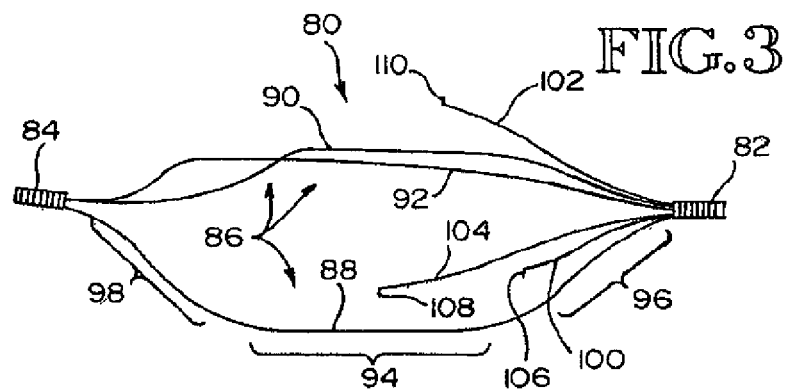
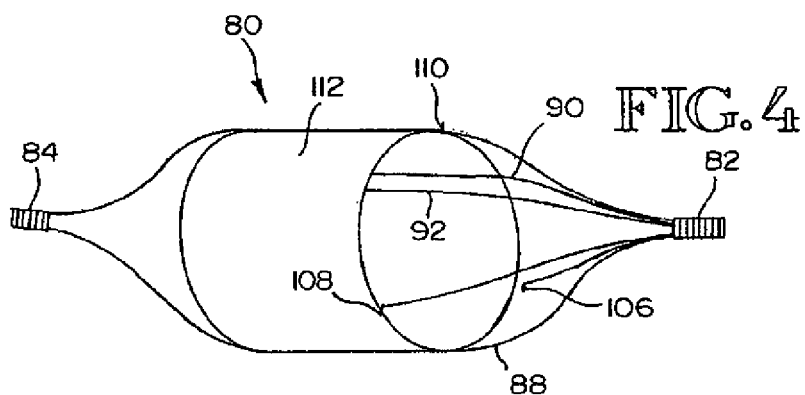
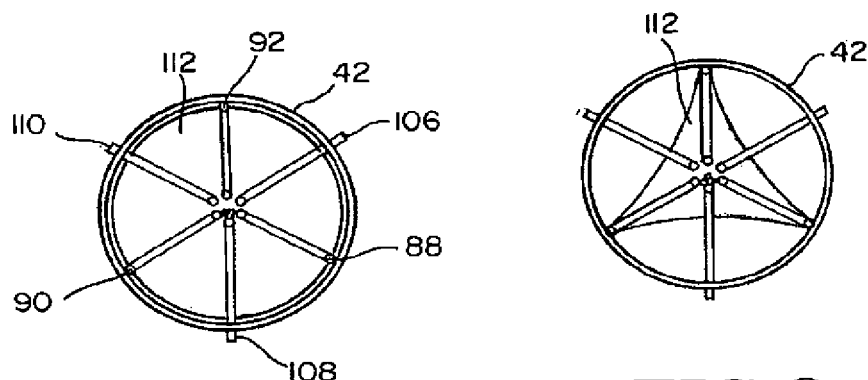

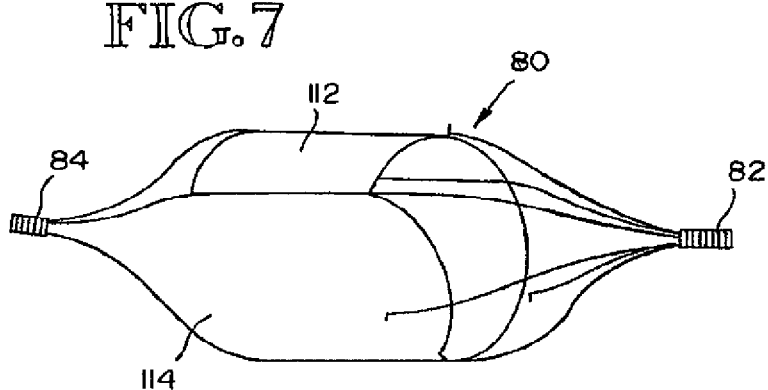
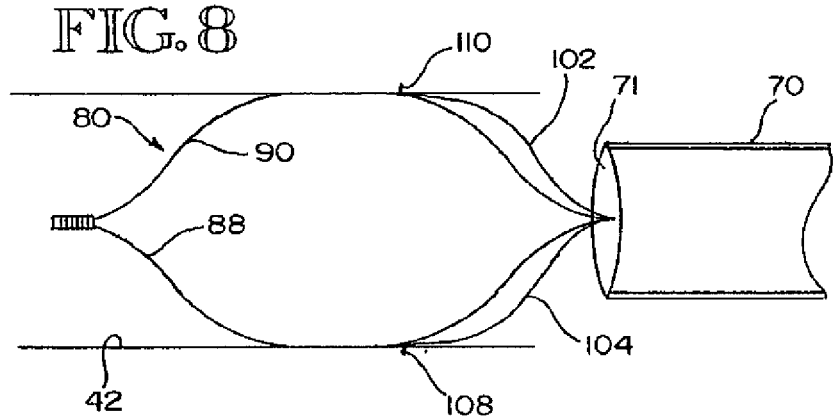
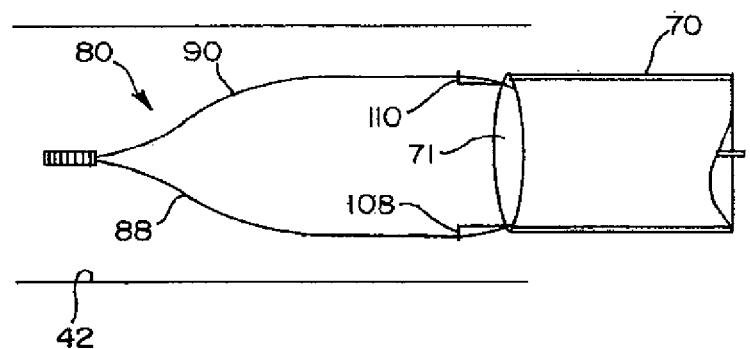

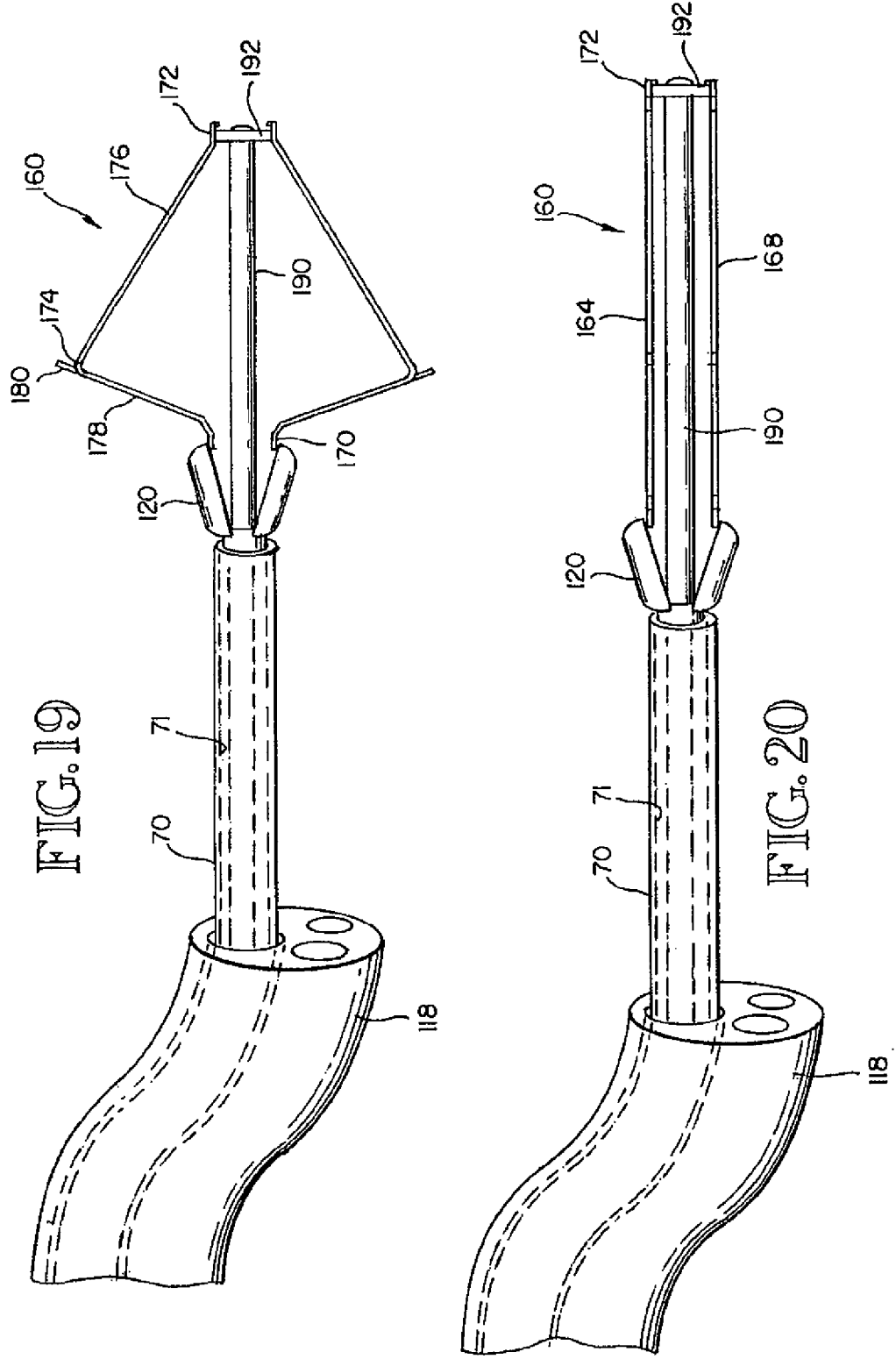

REMOVABLE LUNG REDUCTION DEVICES, SYSTEMS, AND METHODS

CROSS REFERENCE TO RELATED APPLICATIONS

This application is a continuation of U.S. application Ser. No. 12/828,629, filed Jul. 1, 2010, which is a continuation of U.S. application Ser. No. 12/428,287 (now U.S. Pat. No. 7,757,692—issued Jul. 20, 2010), filed Apr. 22, 2009, which is a continuation of U.S. application Ser. No. 10/847,554, filed May 17, 2004, which is a divisional of U.S. application Ser. No. 09/951,105, filed Sep. 11, 2001, each of which is hereby incorporated herein by reference in its entirety. Any and all priority claims identified in the Application Data Sheet, or any correction thereto, are hereby incorporated by reference under 37 CFR 1.57.

BACKGROUND OF THE INVENTION

The present invention is generally directed to a treatment of Chronic Obstructive Pulmonary Disease (COPD). The present invention is more particularly directed to removable air passageway obstruction devices, and systems and methods for removing the devices.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patients whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled .beta.-agonists. For those patients who respond poorly to the foregoing or who have persistent symptoms, Ipratropium bromide may be indicated. Further, courses of steroids, such as corticosteroids, may be required. Lastly, antibiotics may be required to prevent infections and influenza and pheumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopping reimbursing for LVRS. Unfortunately, data is relatively scarce and many factors conspire to make what data exists difficult to interpret. The procedure is currently under review in a controlled clinical trial. What data does exist tends to indicate that patients benefited from the procedure in terms of an increase in forced expiratory volume, a decrease in total lung capacity, and a significant improvement in lung function, dyspnea, and quality of life. However, the surgery is not without potential complications. Lung tissue is very thin and fragile. Hence, it is difficult to suture after sectioning. This gives rise to potential infection and air leaks. In fact, nearly thirty percent (30%) of such surgeries result in air leaks.

Improvements in pulmonary function after LVRS have been attributed to at least four possible mechanisms. These include enhanced elastic recoil, correction of ventilation/perfusion mismatch, improved efficiency of respiratory muscaulature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

In view of the need in the art for new and improved therapies for COPD which provide more permanent results than pharmacotherapy while being less invasive and traumatic than LVRS, at least two new therapies have recently been proposed.

Both of these new therapies provide lung size reduction by permanently collapsing at least a portion of a lung.

In accordance with a first one of these therapies, and as described in U.S. Pat. No. 6,258,100 assigned to the assignee of the present invention and incorporated herein by reference, a lung may be collapsed by obstructing an air passageway communicating with the lung portion to be collapsed. The air passageway may be obstructed by placing an obstructing member in the air passageway. The obstructing member may be a plug-like device which precludes air flow in both directions or a one-way valve which permits air to be exhaled from the lung portion to be collapsed while precluding air from being inhaled into the lung portion. Once the air passageway is sealed, the residual air within the lung will be absorbed over time to cause the lung portion to collapse.

As further described in U.S. Pat. No. 6,258,100, the lung portion may be collapsed by inserting a conduit into the air passageway communicating with the lung portion to be collapsed. An obstruction device, such as a one-way valve is then advanced down the conduit into the air passageway. The obstruction device is then deployed in the air passageway for sealing the air passageway and causing the lung portion to be collapsed.

The second therapy is fully described in copending U.S. application Ser. No. 09/534,244, filed Mar. 23, 2000, for LUNG CONSTRICTION APPARATUS AND METHOD and, is also assigned to the assignee of the present invention. As described therein, a lung constriction device including a sleeve of elastic material is configured to cover at least a portion of a lung. The sleeve has a pair of opened ends to permit the lung portion to be drawn into the sleeve. Once drawn therein, the lung portion is constricted by the sleeve to reduce the size of the lung portion.

Both therapies hold great promise for treating COPD. Neither therapy requires sectioning and suturing of lung tissue.

While either therapy alone would be effective in providing lung size reduction and treatment of COPD, it has recently been proposed that the therapies may be combined for more effective treatment. More specifically, it has been proposed that the therapies could be administered in series, with the first mentioned therapy first applied acutely for evaluation of the effectiveness of lung size reduction in a patient and which lung portions should be reduced in size to obtain the best results. The first therapy is ideal for this as it is noninvasive and could be administered in a physician's office. Once the effectiveness of lung size reduction is confirmed and the identity of the lung portions to be collapsed is determined, the more invasive second mentioned therapy may be administered.

In order to combine these therapies, or simply administer the first therapy for evaluation, it will be necessary for at least some of the deployed air passageway obstruction devices to be removable. Unfortunately, such devices as currently known in the art are not suited for removal. While such devices are expandable for permanent deployment, such devices are not configured or adapted for recollapse after having once been deployed in an air passageway to facilitate removal. Hence, there is a need in the art for air passageway obstruction devices which are removable after having been deployed and systems and methods for removing them.

SUMMARY OF THE INVENTION

The invention provides device for reducing the size of a lung comprising an obstructing structure dimensioned for insertion into an air passageway communicating with a portion of the lung to be reduced in size, the obstructing structure having an outer dimension which is so dimensioned when deployed in the air passageway to preclude air from flowing into the lung portion to collapse the portion of the lung for reducing the size of the lung, the obstructing structure being collapsible to permit removal of the obstruction device from the air passageway.

The invention further provides an assembly comprising a device for reducing the size of a lung, the device being dimensioned for insertion into an air passageway communicating with a portion of the lung to be reduced in size, the device having an outer dimension which is so dimensioned when deployed in the air passageway to preclude air from flowing into the lung portion to collapse the portion of the lung for reducing the size of the lung, a catheter having an internal lumen and being configured to be passed down a trachea, into the air passageway, and a retractor dimensioned to be passed down the internal lumen of the catheter, seizing the device, and pulling the obstruction device proximally into the internal lumen to remove the device from the air passageway. The device is collapsible after having been deployed to permit the device to be pulled proximally into the internal lumen of the catheter by the retractor.

The invention further provides a method of removing a deployed air passageway obstruction device from an air passageway in which the device is deployed. The method includes the steps of passing a catheter, having an internal lumen, down a trachea and into the air passageway, advancing a retractor down the internal lumen of the catheter to the device, seizing the device with the retractor, collapsing the device to free the device from deployment in the air passageway, and pulling the device with the retractor proximally into the internal lumen of the catheter.

The invention still further provides an air passageway obstruction device comprising a frame structure, and a flexible membrane overlying the frame structure. The frame structure is collapsible upon advancement of the device into the air passageway, expandable into a rigid structure upon deployment in the air passageway whereby the flexible membrane obstructs inhaled air flow into a lung portion communicating with the air passageway, and re-collapsible upon removal from the air passageway.

The invention still further provides an air passageway obstruction device comprising frame means for forming a support structure, and flexible membrane means overlying the support structure. The frame means is expandable to an expanded state within an air passageway to position the membrane means for obstructing air flow within the air passageway and is collapsible for removal of the device from the air passageway.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

FIG. 3 is a perspective view, illustrating the frame structure of a removable air passageway obstruction device embodying the present invention;

FIG. 4 is a perspective view of the complete air passageway obstruction device of FIG. 3;

FIG. 5 is an end view of the device of FIG. 3 illustrating its operation for obstructing inhaled air flow;

FIG. 6 is another end view of the device of FIG. 3 illustrating its operation for permitting exhaled air flow;

FIG. 7 is a perspective view of the device of FIG. 3, illustrating its operation for permitting partial exhaled air flow;

FIG. 8 is a side view illustrating a first step in removing the device of FIG. 3 in accordance with one embodiment of the present invention;

FIG. 9 is another side view illustrating the collapse of the device of FIG. 3 as it is removed from an air passageway;

FIG. 19 is a side view illustrating an intermediate step in the removal of the device of FIG. 15; and FIG. 20 is a side view illustrating the collapse of the device of FIG. 15 during its removal from an air passageway.

DETAILED DESCRIPTION OF THE PREFERRED EMBODIMENTS

Figure 1:
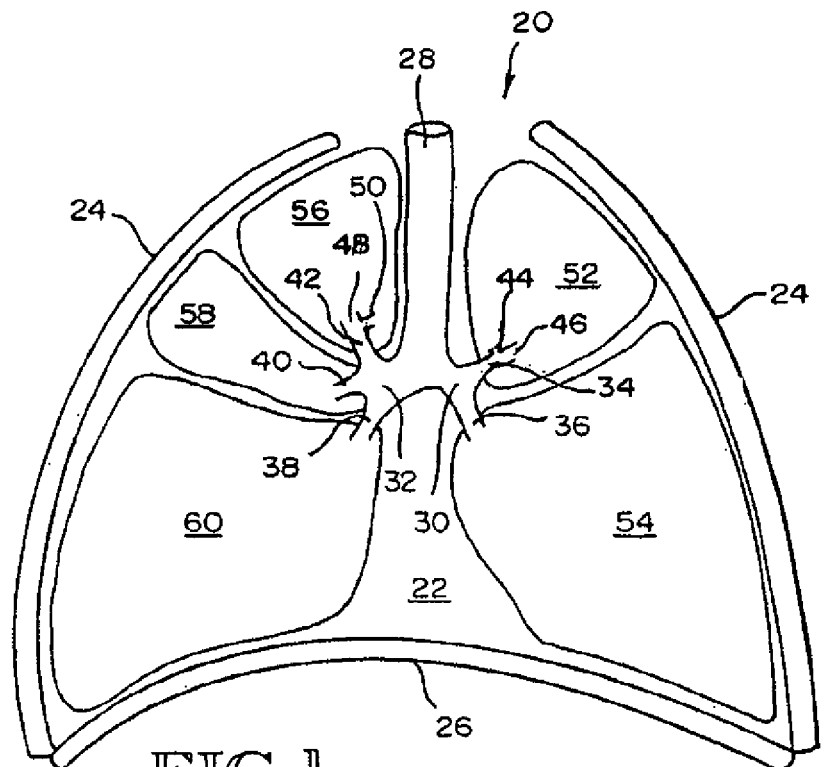
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
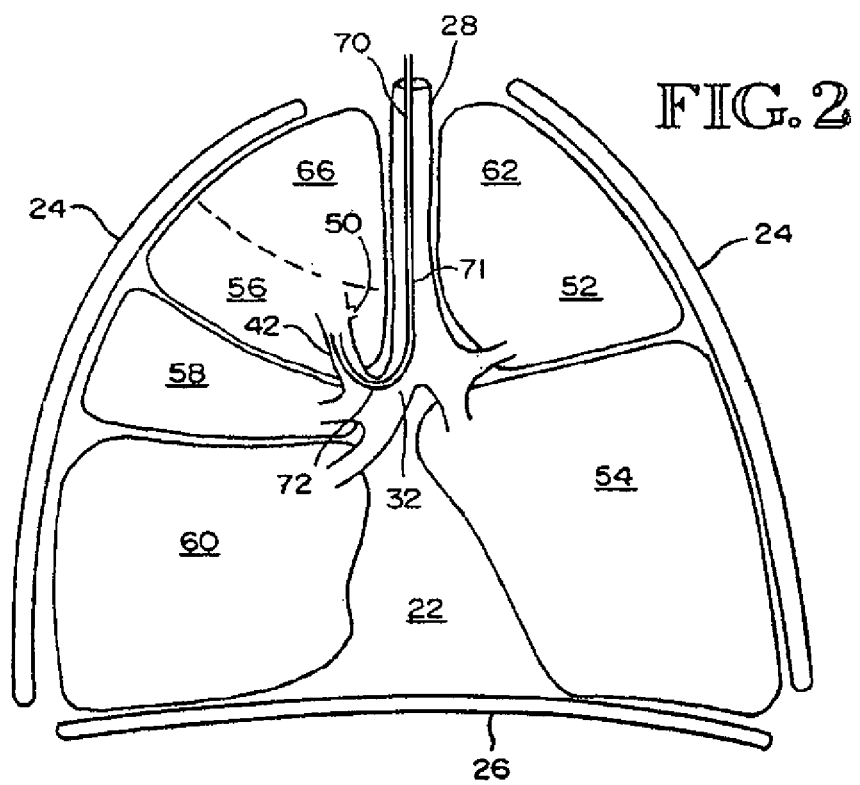
FIG. 2 is a sectional view similar to FIG. 1 but illustrating a respiratory system suffering from COPD and the execution of a first step in treating the COPD condition in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving the diaphragm 28. Instead, in order to create the negative pressure in the thorax 22 required for breathing, this individual must move the chest wall outwardly to increase the volume of the thorax. This results in inefficient breathing causing these individuals to breathe rapidly with shallow breaths. It has been found that the apex portion 62 and 66 of the upper lung lobes 52 and 56, respectively, are most affected by COPD.

In accordance with this embodiment of the present invention, COPD treatment or evaluation is initiated by feeding a conduit or catheter 70 down the trachea 28, into a mainstream bronchus such as the right mainstem bronchus 32, and into an air passageway such as the bronchial branch 42 or the bronchial sub-branch 50. An air passageway obstruction device embodying the present invention is then advanced down an internal lumen 71 of the catheter 70 for deployment in the air passageway. Once deployed, the obstruction device precludes inhaled air from entering the lung portion to be collapsed. In accordance with the present invention, it is preferable that the obstruction device take the form of a one-way valve. In addition to precluding inhaled air from entering the lung portion, the device further allows air within the lung portion to be exhaled. This results in more rapid collapse of the lung portion. However, obstruction devices which preclude both inhaled and exhaled air flow are contemplated as falling within the scope of the invention.

The catheter 70 is preferably formed of flexible material such as polyethylene. Also, the catheter 70 is preferably preformed with a bend 72 to assist the feeding of the catheter from the right mainstem bronchus 32 into the bronchial branch 42.

FIGS. 3 and 4 show an air passageway obstruction device 80 embodying the present invention. The device 80 includes a proximal end 82 and a distal end 84. The device 80 further includes a frame structure 86 including frame supports 88, 90, and 92.

Each of the frame supports has a shape to define a generally cylindrical center portion 94 and a pair of oppositely extending inwardly arcuate conical end portions 96 and 98. The frame structure further includes a plurality of fixation members 100, 102, and 104 which extend distally from the proximal end 82. The fixation members have the generally conical shape and terminate in fixation projections or anchors 106, 108, and 110 which extend radially outwardly.

Overlying and partially enclosing the frame structure 86 is a flexible membrane 112. The flexible membrane extends over the generally cylindrical and conical portions 94 and 98 defined by the frame structure. Hence, the flexible membrane is opened in the proximal direction.

The flexible membrane may be formed of silicone or polyurethane, for example. It may be secured to the frame structure in a manner known in the art such as by crimping, riveting, or adhesion.

The frame structure 86 and the device 80 are illustrated in FIGS. 3 and 4 as the device would appear when fully deployed in an air passageway. The frame structure supports and frame structure fixation members are preferably formed of stainless steel or Nitinol or other suitable material which has memory of an original shape. The frame structure permits the device to be collapsed for advancement down the internal lumen 71 of the catheter 70 into the air passageway where the device is to be deployed. Once the point of deployment is reached, the device is expelled from the catheter to assume its original shape in the air passageway. In doing so, the generally cylindrical portion 94 contacts the inner wall of the air passageway and the fixation projections 106, 108, and 110 pierce the wall of the air passageway for fixing or anchoring the device 80 within the air passageway.

When the device 80 is deployed, the frame structure 86 and flexible membrane 112 form an obstructing structure or one-way valve. FIGS. 5 and 6 show the valve action of the device 80 when deployed in an air passageway, such as the bronchial branch 42.

As shown in FIG. 5, during inhalation, the flexible membrane is filled with air and expands outwardly to obstruct the air passageway 42. This precludes air from entering the lung portion being collapsed. However, as shown in FIG. 6, during expiration, the flexible membrane 112 deflects inwardly to only partially obstruct the air passageway 42. This enables air, which may be in the lung portion being collapsed, to be exhaled for more rapid collapse of the lung portion. FIG. 7 is another view showing the device 80 during expiration with a portion 114 of the membrane 112 deflected inwardly.

FIGS. 8 and 9 illustrate a manner in which the device 80 may be removed from the air passageway 42 in accordance with one embodiment of the present invention. As previously mentioned, it may be desired to remove the device 80 if it is only used for evaluating the effectiveness of collapsing a lung portion or if it is found the more effective treatment may be had with the collapse of other lung portions.

The device 80 is shown in FIG. 8 in a fully deployed state. The catheter 70 having the internal lumen 71 is advanced to the proximal end of the device 80. In FIG. 8 it may be noted that the fixation members 102 and 104 define a larger conical radius than the frame supports 88 and 90. Hence, when the proximal end of the device is engaged by a retractor and the catheter 70 is moved distally as shown in FIG. 9, the internal lumen of the catheter engages the fixation members 102 and 104 before it engages the frame supports 88 and 90. This causes the fixation projections to first disengage the inner wall of the air passageway 42. With the device now free of the air passageway side wall, the retractor may be used to pull the device into the internal lumen 71 of the catheter 70 causing the support structure and thus the device to collapse. The collapsed device may now fully enter the internal lumen of the catheter for removal.

Figure 10:
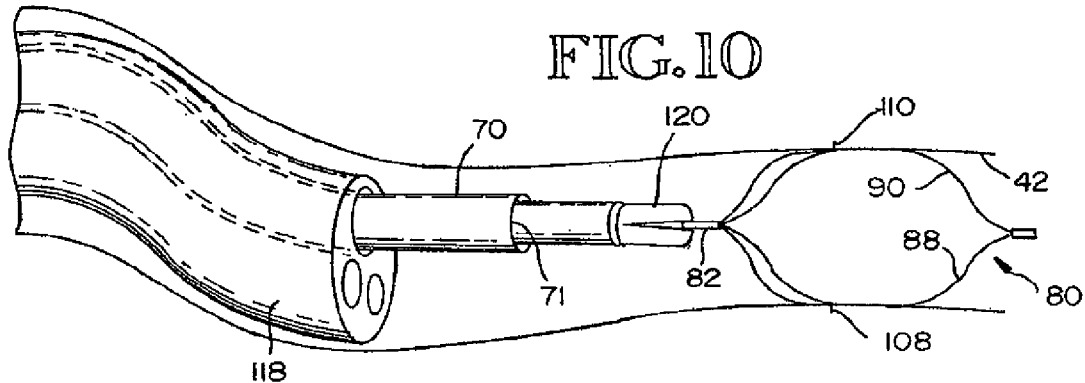
FIG. 10 is a side view illustrating an initial step in the removal of the device of FIG. 3 in accordance with another embodiment of the present invention.
Figure 11:
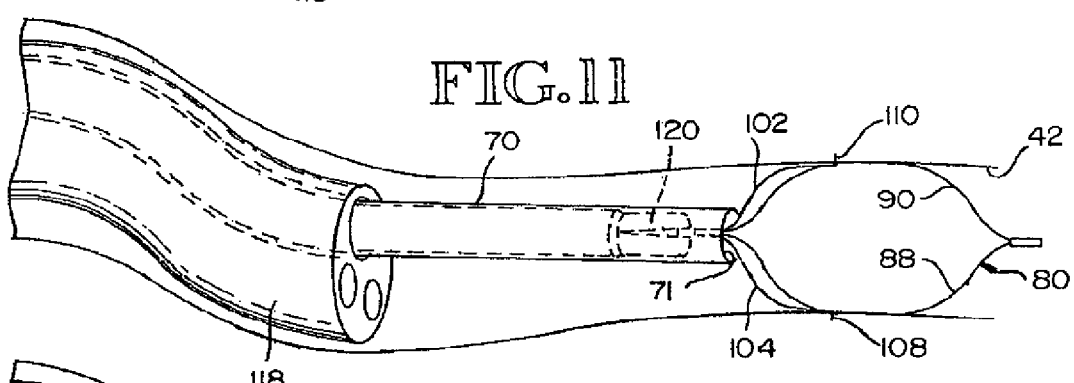
FIG. 11 is a side view illustrating engagement of the frame structure of the device with a catheter during removal of the device.
Figure 12:
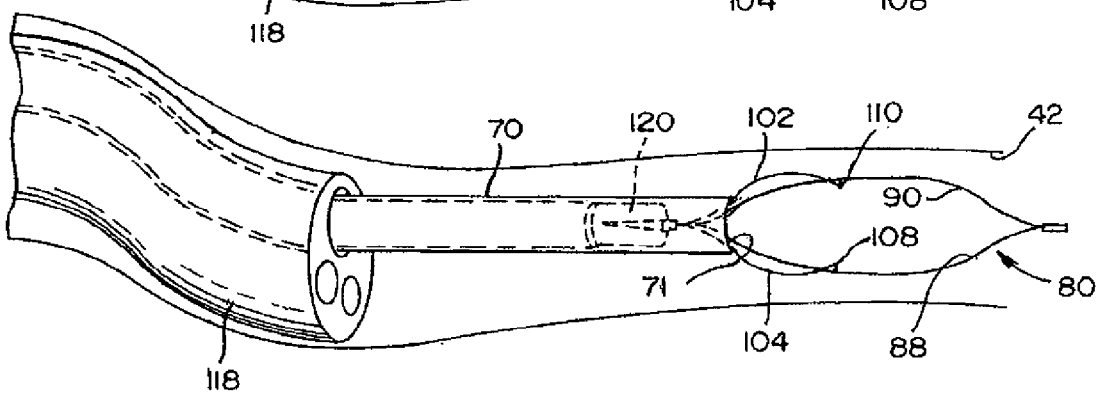
FIG. 12 is a side view illustrating the collapse of the device by the catheter during removal of the device.

FIGS. 10-12 show another embodiment of the present invention for removing the device 80 from the air passageway 42. Here, the catheter 70 is fed down a bronchoscope 118 to the device 80. The retractor takes the form of a forceps 120.

In FIG. 10 it may be seen that the forceps has just engaged the proximal end 82 of the device 80. In FIG. 11 the forceps 120 is held stationary while the catheter 70 is advanced distally so that the internal lumen 71 of the catheter 70 engages the fixation members 102 and 104. Further advancement of the catheter 70 as seen in FIG. 12 deflects the fixation projections 110 and 108 inwardly away from the inner wall of the air passageway 42. Now, the forceps may be used to pull the device 80 into the internal lumen 71 of the catheter 70 for removal of the device 80 from the air passageway 42.

Figure 13:
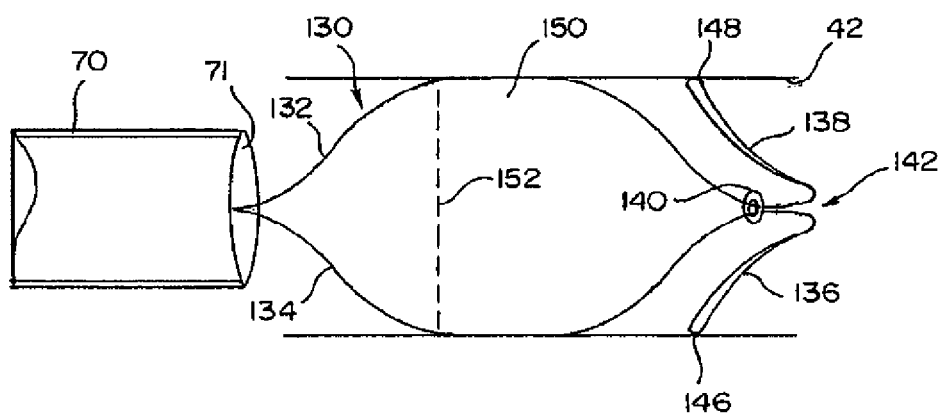
FIG. 13 is a side view of another air passageway obstruction device embodying the present invention during an initial step in its removal from an air passageway.
Figure 14:
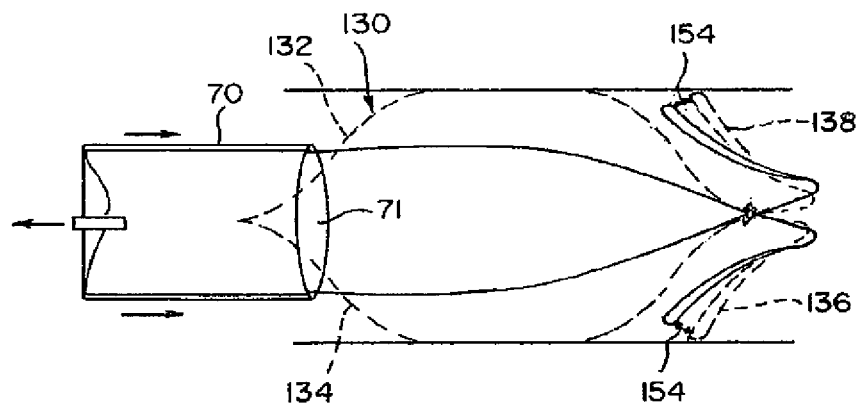
FIG. 14 is another side view of the device of FIG. 13 illustrating its collapse during removal from the air passageway.

FIGS. 13 and 14 show another removable air passageway obstruction device 130 and a method of removing it from an air passageway in accordance with the present invention. The device 130 is shown in FIG. 13 deployed in the air passageway 42 and the catheter 70 is in ready position to remove the device 130 from the air passageway 42.

The device 130 is of similar configuration to the device 80 previously described. Here however, the fixation members 136 and 138 are extensions of the frame supports 132 and 134, respectively. To that end, it will be noted in FIG. 13 that the frame supports 132 and 134 cross at a pivot point 140 at the distal end 142 of the device 130. They extend distally and then are turned back at an acute angle to terminate at fixation or anchor ends 146 and 148. When the device is deployed as shown in FIG. 13, the cylindrical portions of the support frame engage the inner wall of the air passageway 42 and the fixation points 146 and 148 project into the inner wall of the air passageway 42 to maintain the device in a fixed position. The flexible membrane 150 extends from the dashed line 152 to the pivot or crossing point 140 of the frame supports 132 and 134 to form a one-way valve.

When the device is to be removed, the frame structure of the device 130 is held stationary by a retractor within the catheter 70 and the catheter is advanced distally. When the catheter 70 engages the frame supports 132 and 134, the frame supports are deflected inwardly from their dashed line positions to their solid line positions. This also causes the fixation members 136 and 138 to be deflected inwardly from their dashed line positions to their solid line positions in the direction of arrows 154. These actions disengage the device 130 from the inner wall of the air passageway 42. Now, the retractor may pull the device into the internal lumen 71 of the catheter 70 for removal of the device 130 from the air passageway 42.

Figure 15:
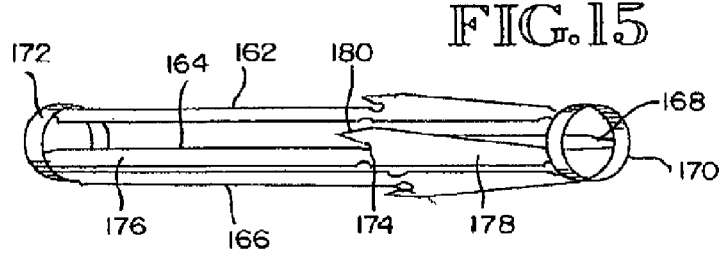
FIG. 15 is a perspective view of the frame structure of another removable air passageway obstruction device embodying the present invention.
Figure 16:
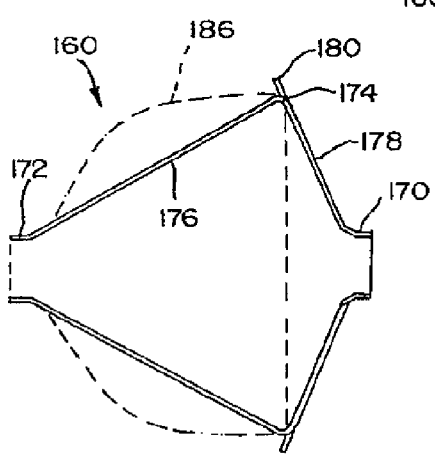
FIG. 16 is a cross-sectional side view of the device of FIG. 15 shown in a deployed state.
Figure 17:
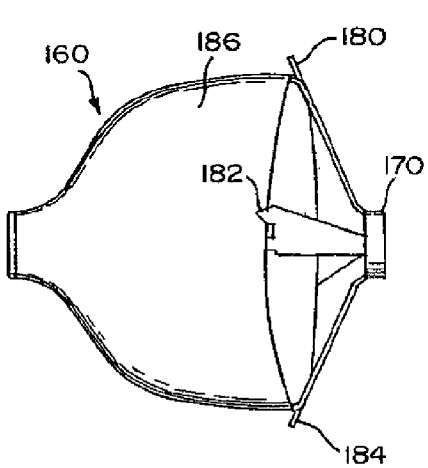
FIG. 17 is a perspective side view of the device of FIG. 15 shown in a deployed state.

FIGS. 15-17 show a still further removable air passageway obstruction device 160 embodying the present invention. As shown in the initial collapsed state in FIG. 15, the device 160 includes a plurality of frame supports 162, 164, 166, and 168. The frame supports extend between a proximal ring 170 and a distal ring 172. The device 160 is preferably laser cut from a sheet of Nitinol.

Since each of the frame supports are identical, only frame support 164 will be described herein. As will be noted, the support 164 includes a bend point 174 with a relatively long section 176 extending distally from the bend point 174 and a relatively short section 178 extending proximally from the bend point 174. The short section 178 includes a fixation projection or anchor 180 extending slightly distally from the bend point 174.

FIGS. 16 and 17 show the device 160 in its deployed configuration. When the device is deployed, it is advanced down a catheter to its deployment site in its collapsed state as shown in FIG. 15. When the deployment site is reached, the device 160 is held outside of the catheter and the rings 170 and 172 are pulled toward each other. This causes the device to bend at the bend points of the frame supports. This forms fixation projections 180, 182, and 184 extending into the inner wall of the air passageway to fix the device in position.

The relatively long sections of the frame supports are covered with a flexible membrane 186 as shown in FIGS. 16 and 17 to form a one-way valve. The valve functions as previously described to obstruct inhaled air flow but to permit exhaled air flow.

Figure 18:
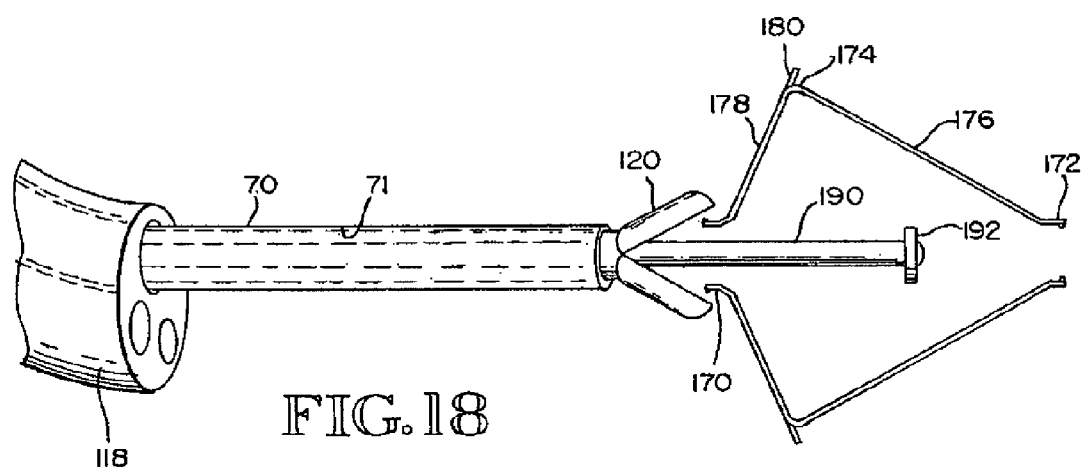
FIG. 18 is a side view illustrating an initial step in removing the device of FIG. 15 from an air passageway.

FIGS. 18-20 illustrate a manner of removing the device 160 from an air passageway. Once again a catheter 70 is advanced down a bronchoscope 118 to the device 160. Next, a retractor including a forceps 120 and pin 190 are advanced to the device. The pin 190, carrying a larger diameter disk 192, extends into the device as the forceps 120 grasps the proximal ring 170 of the device 160. The pin 190 continues to advance until the disk 192 engages the distal ring 172 of the device 160 as shown in FIG. 19. Then, while the forceps 120 holds the proximal ring 170, the pin 190 and disk 192 are advanced distally carrying the distal ring 172 distally. This causes the device 160 to straighten and collapse as shown in FIG. 20. Now, the forceps 120, pin 190, and the device 160 may be pulled into the internal lumen 71 of the catheter 70 for removal of the device. As will be appreciated by those skilled in the art, the foregoing steps may be reversed for deploying the device 160.

While particular embodiments of the present invention have been shown and described, modifications may be made, and it is therefore intended in the appended claims to cover all such changes and modifications which fall within the true spirit and scope of the invention.

What is claimed is:

1. A device for insertion into a lung airway passage, the device having a proximal end and a distal end and comprising:
    a plurality of elongate frame supports configured to transition between a collapsed configuration and an expanded configuration, one or more of the frame supports having:
        an anchor portion comprising a piercing portion configured to pierce an airway wall and a bent portion configured to limit a depth to which the piercing portion pierces an airway wall, the piercing portion extending from a bifurcated portion of the anchor portion; and a membrane support portion connected to the anchor portion, the membrane support portion having a convex side and a concave side;

a flexible membrane forming a one-way valve and having an axial centerline and overlaying at least a portion of the convex side of the membrane support portion; and a ring member, the anchor portion connected to the ring member and extending from the ring member in a distal direction away from the axial centerline when the elongate frame supports are in the expanded configuration.

2. The device of claim 1, wherein the flexible membrane has an open proximal end and a closed distal end.

3. The device of claim 1, wherein the flexible membrane permits passage of airflow in a proximal direction and obstructs airflow in a distal direction.

4. The device of claim 1, wherein a length of the anchor portion parallel to the axial centerline increases when the elongate frame supports transition from the expanded configuration to the collapsed configuration.

5. The device of claim 1, wherein a radial length of the anchor portion perpendicular to the axial centerline decreases when the elongate frame supports transition from the expanded configuration to the collapsed configuration.

6. The device of claim 1, wherein the device fits within a working portion of a catheter when the elongate frame supports are in the collapsed configuration.

7. The device of claim 1, wherein a proximal end of each membrane support portion curves toward the axial centerline.

8. A medical device for treating lung conditions, the medical device comprising:

an occlusion portion having an open proximal end and a closed distal end, the occlusion portion comprising:

a plurality of frame members having a convex side and a concave side; and a flexible membrane forming a one-way valve and overlaying at least a portion of the convex side of the frame members; and an anchor portion connected to the occlusion portion and comprising:

an ring member; and a plurality of anchors extending from the ring member in a distal direction, one or more of the anchors comprising a piercing tip extending from a bifurcated portion of the anchor portion and a bent portion, the bent portion limiting a depth to which the piercing tip pierces an airway wall when the medical device is deployed in an airway passage.

9. The medical device of claim 8, wherein the occlusion portion is configured to transition between an occluding configuration and a collapsed configuration.

10. The medical device of claim 8, wherein the anchors engage with walls of an airway passage to inhibit movement of the medical device in the airway passage when the device is deployed in the airway passage.

11. The medical device of claim 8, wherein each of the piercing tips extends from a bifurcated portion of the one or more the anchors.

12. The medical device of claim 8, wherein the occlusion portion has an axial centerline.

13. The medical device of claim 8, wherein the medical device fits within a catheter when in a collapsed configuration.

14. The medical device of claim 8, wherein the flexible membrane is positioned at least partially on an outer surface of the frame members.

15. The medical device of claim 8, wherein the open proximal end of the occlusion portion engages with airway wall when the medical device is deployed in an airway passage.

16. The medical device of claim 8, wherein the occlusion portion partially collapses to permit airflow in a proximal direction when the medical device is deployed in an airway passage.

17. The medical device of claim 8, wherein a proximal end of each of the frame members bends toward an axial centerline of the occlusion portion.

* * * * *